United States Patent [19]

Smith et al.

[11] 4,172,097

[45] Oct. 23, 1979

[54] PRODUCTION OF PROPIOPHENONE

[75] Inventors: Charles A. Smith; Louis F. Theiling, Jr., both of Charleston, W. Va.

[73] Assignee: Union Carbide Corporation, New York, N.Y.

[21] Appl. No.: 936,843

[22] Filed: Aug. 25, 1978

[51] Int. Cl.² ............................................. C07C 45/18
[52] U.S. Cl. ................................... 260/592; 260/595
[58] Field of Search ................... 260/593 R, 595, 592

[56] References Cited

U.S. PATENT DOCUMENTS

| | | | |
|---|---|---|---|
| 2,612,524 | 9/1952 | Zettlemoyer et al. | 260/595 |
| 2,697,729 | 12/1954 | Ohlson et al. | 260/595 |
| 3,468,956 | 9/1969 | Mead | 260/595 |
| 3,643,852 | 7/1972 | Mills | 260/595 |

OTHER PUBLICATIONS

Neunhoeffer et al., Chem. Ber., vol. 72, pp. 919-929 (1939).

*Primary Examiner*—James H. Reamer
*Attorney, Agent, or Firm*—Franklyn Schoenberg

[57] ABSTRACT

In the production of propiophenone by a vapor-phase, cross-decarboxylation process, an undesirable by-product, isobutyrophenone, is suppressed by addition of water or steam to the reactant stream.

9 Claims, No Drawings

PRODUCTION OF PROPIOPHENONE

BACKGROUND OF THE INVENTION

This invention pertains to the production of propiophenone by a vapor-phase, cross-decarboxylation process and more particularly to the suppression of by-product formation.

Propiophenone is used as a starting material in pharmaceutical applications particularly for the manufacture of dextropropoxyphene or alpha-d-4-dimethylamino-3-methyl-1,2-diphenyl-2-butanol propionate. Propiophenone can be produced by a Friedel-Crafts reaction of benzene and propionic acid, propionic anhydride or propionyl chloride catalyzed by Lewis acids. Although Friedel-Crafts processes produce no significant amounts of aromatic ketone by-products, such processes suffer from very high costs involved in corrosion of production facilities and waste disposal required for environmental protection.

An attractive alternative synthesis of propiophenone and other specialty ketones utilizes a vapor-phase cross-decarboxylation process. In the case of propiophenone, benzoic acid is reacted with propionic acid at high temperatures over a catalyst. Propiophenone, diethyl ketone, carbon dioxide, and water are the major products. Numerous by-products are also formed in small amounts, including other dialkyl ketones, other phenylalkyl ketones and biphenol. One of the by-products produced in the vapor-phase process is isobutyrophenone. Depending upon the process conditions used, isobutyrophenone production may equal 10 percent or more of the propiophenone production. Separation of isobutyrophenone from propiophenone is impossible using conventional distillation techniques, inasmuch as the boiling points of these two compounds are within 1° C. of each other. Other separation techniques, such as fractional crystallization or extractive distillation are costly and have not been perfected for this particular separation problem.

Dextropropoxyphene is used medically as an analgesic. Drug dependence associated with its use has been found to be uncommon. Unfortunately, its isomer prepared from isobutyrophenone rather than propiophenone has been found to be an addictive narcotic. Therefore, it is essential that propiophenone used for the preparation of dextropropoxyphene be of high purity such that the isobutyrophenone content shall be as low as possible.

It is therefore an object of this invention to provide a vapor-phase, cross-decarboxylation synthesis for the preparation of alkyl aryl ketones with a minimum of by-products.

It is a specific object of this invention to prepare propiophenone by the catalytic vapor-phase cross-decarboxylation of benzoic acid with propionic acid, in which the content of the by-product isobutyrophenone is held to a minimum.

SUMMARY OF THE INVENTION

In the process for the production of propiophenone by the catalytic, vapor-phase cross-decarboxylation of an aromatic carboxylic acid having 6 to about 14 carbon atoms with propionic acid, an improvement has been devised whereby the formation of by-products is suppressed which comprises introducing at least about 0.5 to 25 moles of water or a secondary alcohol having 3 to about 6 carbon atoms per mole of aromatic carboxylic acid into a feed stream comprising a mole ratio of aromatic carboxylic acid: propionic acid of about 1:1 to about 1:10 prior to the entrance of said feed stream into a reaction zone maintained at a temperature of about 400° C. to about 600° C.

The preferred aromatic carboxylic acid used in this invention is benzoic acid although other aromatic carboxylic acids such as benzoic acid alkyl substituted derivatives where the alkyl group contains 1 to about 4 carbon atoms can also be used.

It is preferred to use about 4 to about 8 moles of water or secondary alcohol per mol of aromatic carboxylic acid. Of the two, water is the preferred modifying agent. The preferred secondary alcohol is isopropanol although other secondary alcohols such as 2-butanol, 2 or 3-pentanol, 2 or 3-hexanol can also be used if desired. In this regard it is surprising that primary alcohols and particularly methanol, ethanol, n-propanol, n-butanol, isobutanol and the like have a deleterious effect on the generation of the by-product isobutyrophenone.

It is preferred to use a ratio of aromatic carboxylic acid to propionic acid of about 1:2 to about 1:4.

The preferred reaction temperature is about 440° to about 520° C.

The nature of the catalyst used in this reaction is not critical. Thus, although calcium acetate supported on alumina has been found to serve satisfactorily, other catalysts which can be used include cobalt acetate, manganous oxide, and the like. It is preferred to use superatmospheric pressure of about 10 to about 100 psig but this is not critical and other pressures above and below atmospheric pressure as well as atmospheric pressure can be used if desired.

No special equipment is needed other than that known to those skilled in the art for handling materials and reactions at high temperature, means for supporting a catalytic bed in a high temperature reactor, and metering means for introducing reaction stream and withdrawing product.

Residence time is not narrowly critical. It has been found convenient to use a residence time of about 0.4–1.0 grams of reactants per gram of catalyst per hour.

Although the ratio of reactor surface to reactor volume is not critical, it was found that in some instances a slight depressing effect on the formation of isobutyrophenone resulted by increasing the surface to volume ratio by 55 percent by dispersing pieces of stainless steel tubing in the catalyst bed.

Isopropanol is more effective on a molar basis than steam in suppressing isobutyrophenone formation but is more expensive. Steam can be used to virtually eliminate isobutyrophenone by-product formation by adding steam to a propionic acid:benzoic acid feed stream.

The invention can be practiced as a batch or continuous system with the latter being more efficient.

The reactions involved in this invention are dilineated in the equation shown below:

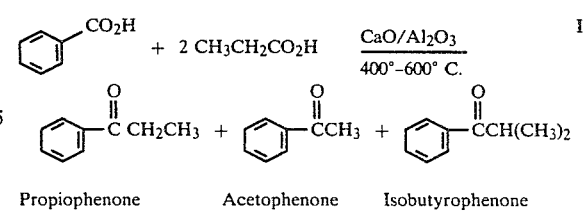

-continued

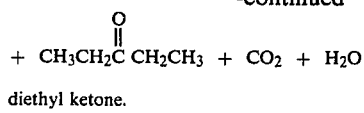

diethyl ketone.

The invention is further described in the Examples which follow. All parts and percentages are by weight unless otherwise specified.

EXAMPLE 1

The reactor used for the preparation of propiophenone in accordance with this invention consisted of a reactor fabricated from 1-inch by 48-inch stainless steel pipe, insulated and electrically heated. Temperatures were determined at four points by thermocouples positioned in a ¼" thermowell which extended through the entire length of the reactor.

Reactants were fed, via a small diaphram pump from a calibrated feed tank through a steam-jacketed line to the top of the reactor. The feed tank and pump were warmed by infrared heat lamps to prevent crystallization of benzoic acid.

The catalyst bed consisted of two layers. A 13" bed of inert material in the top end of the vertically oriented reactor served as a preheat section. The bottom 31" consisted of calcium acetate on alumina.

Activated alumina (Alcoa F-1 grade, 4-8 mesh) is immersed in a 25 percent aqueous solution of calcium acetate for 2 to 24 hours. The calcium acetate solution is drained off, and most of the excess water adhering to the alumina is removed by vacuum evaporation. The impregnated catalyst is then heated overnight at 500° C. to remove the last traces of water. The amount of calcium impregnated on the catalyst depends on how long the alumina is dipped in the calcium acetate solution and on how many times the procedure is repeated. The catalyst used in these examples contained 2.95 percent calcium by weight (3.87 percent by weight when calculated as calcium oxide).

The reactants consisted of a 2:1 mole ratio of propionic and benzoic acids, with water or secondary alcohol diluent added as indicated in Table I. Controls A and C where no diluent was used and Control B where methanol was used are also shown in Table I.

TABLE I

PROPIOPHENONE SUPPRESSION
OF ISOBUTYROPHENONE CO-PRODUCTION

Effect of Water

| Example | S/V Ratio [1] | Diluent Ratio [2] | Isobutyrophenone Production[3] | Acetophenone Production[3] |
|---|---|---|---|---|
| Control A | 4.0 | 0 | 5.04 | 13.2 |
| 1 | 4.0 | 4 | 4.68 | 18.3 |
| 2 | 4.0 | 8 | 2.31 | 18.9 |
| 3 | 4.0 | 1(iPrOH) | 3.19 | 23.3 |
| Control B | 4.0 | 1(MeOH) | 10.43 | 13.4 |
| Control C | 6.2 | 0 | 6.40 | 18.2 |
| 4 | 6.2 | 1 | 4.68 | 18.5 |
| 5 | 6.2 | 4 | 3.53 | 22.1 |
| 6 | 6.2 | 8 | 2.75 | 25.2 |

[1]Surface-to-volume ratio of the reactor.
[2]Moles of diluent per mole of benzoic acid in the feed stream. The diluent is water unless otherwise specified.
[3]Pounds per pound of propiophenone produced.

In Example 1, using the reactor described above, together with ancillary equipment, a mixture containing 2 moles of propionic acid per mole of benzoic acid was fed to the reactor together with 4 moles of water per mole of benzoic acid at a rate of 249 ml/hr. for 4.5 hours. The reaction temperature was maintained between 445° C. and 450° C. Analysis of the condensed organic layer by gas chromatography indicated that 4.68 pounds of isobutyrophenone were produced per 100 pounds of propiophenone. These data are delineated in Table I. The instrument used was a Bendix Model 2300 dual column programmed temperature gas chromatograph having a thermal conductivity detector. The bridge current was 200 ma. with a 0-1 mv. recorder. The column consisted of two, 10 feet by ⅛ inch stainless steel tubing packed with silicone on an inert support. The column temperature was 190° C. The carrier gas was helium at 30 cc/minute.

CONTROL A

Example 1 was repeated except that no water was present in the feed mixture fed to the reactor; the feed rate was 279 ml/hr, the reaction time was 5.5 hours. Analysis of the condensed organic layer by gas chromatography indicated that 5.04 pounds of isobutyrophenone were produced per 100 pounds of propiophenone.

EXAMPLE 2

Example 1 was repeated except that the reactant mixture contain 8 moles of water per mole of benzoic acid and feed rate was 292 ml/hr. After 5 hours, production of isobutyrophenone was 2.31 pounds per 100 pounds of propiophenone as demonstrated by gas chromatographic analysis.

EXAMPLE 3

Example 1 was repeated except that the reactant mixture contained 1 mole of isopropanol per mole of benzoic acid and the feed rate was 214 ml/hr. After 6.5 hours, production of isobutyrophenone was 3.19 pounds per 100 pounds of propiophenone as shown by gas chromatographic analysis.

CONTROL B

Example 1 was repeated with the exception that the reactant mixture contained 1 mole of methanol per mole of benzoic acid and the feed rate was 269 ml/hr. After 4 hours, analysis by gas chromatography indicated the production rate of isobutyrophenone was 10.43 pounds per 100 pounds of propiophenone.

In Examples 1 to 3 and Controls A and B, the ratio of the surface area to the volume of the stainless steel reaction tube was 4.0 m$^2$/m$^3$.

CONTROL C

Control A was repeated with the exception that the ratio of the surface area to volume of the stainless steel reaction tube was increased to 6.2 m$^2$/m$^3$ by dispersing small pieces of ⅛ inch stainless steel tubing in the catalyst bed and the feed rate was 281 ml/hr. The production of isobutyrophenone, as determined by gas chromatographic analysis was 6.40 pounds per 100 pounds of propiophenone.

EXAMPLE 4

Example 1 was repeated except that the reactant mixture contains 1 mole of water per mole of benzoic acid, the feed rate was 285 ml/hr, and the ratio of the surface area to volume of the stainless steel reaction tube was increased to 6.2 m$^2$/m$^3$ by dispersing small pieces of ⅛ inch stainless steel tubing in the catalyst bed.

Production of isobutyrophenone as determined by gas chromatographic analysis was 4.68 pounds per 100 pounds propiophenone.

EXAMPLE 5

Experiment 1 was repeated except that the feed rate was 276 ml/hr, and the surface area to the volume of the stainless steel tube reaction was increased to 6.2 m²/m³ by dispersing small pieces of ⅛ inch stainless steel tubing in the catalyst bed. Analysis by gas chromatography indicated that the production of isobutyrophenone was 3.53 pounds per 100 pounds of propiophenone.

EXAMPLE 6

Example 2 was repeated with the exception that the surface area to volume of the stainless steel reaction tube was increased to 6.2 m²/m³ by dispersing small pieces of ⅛ inches stainless steel tubing in the catalyst bed. Production of isobutyrophenone as determined by gas chromatographic analysis was 2.75 pounds per 100 pounds of propiophenone.

EXAMPLE 7

In a plant scale run, a charge consisting of propionic acid, benzoic acid and steam was charged to a vaporizer at a rate of 625 lbs/hr., 375 lbs/hr., and 175 lbs/hr., respectively. This mixture exited from the vaporizer at a temperature of 135° C. The vaporized charge was heated in a preheater to 325° C. and thence to the first of three catalyst bed zones maintained at a temperature of 470° C. The catalyst was calcium acetate on alumina. The stream of reactants and products was led from the first to the second catalyst bed zone maintained at a temperature of 490° C., together with steam at 0 to 25 lbs/hr. The second catalyst zone effluent was passed to the third catalyst bed zone maintained at a temperature of 510° C., together with steam at a rate of 25–50 lbs/hr. Analysis of the organic layer of the product mixture by gas chromatography indicated the following:

Diethyl ketone—43–44%
Propiophenone—54–56%
Acetophenone—0.5–1.0%
Isobutyrophenone—0–0.15%
Butyrophenone—0

The following conclusions can be drawn from an examination of the experimental data. Co-production of isobutyrophenone on a laboratory scale decreased steadily as the water concentration in the feed stream was increased. Addition of 8 moles of water per mole of benzoic acid resulted in an isobutyrophenone content of 2.3–2.8 percent based on contained propiophenone. With no water, isobutyrophenone production increased to 5.0–6.4 percent.

Addition of isopropanol at ratio of 1 mole per mole of benzoic acid to the mixed acid feed gave low production of isobutyrophenone (3.2 percent) while methanol at the same level showed exactly the opposite trend affording 10.4 percent isobutyrophenone. This demonstrated the unexpected finding that whereas secondary aliphatic alcohols suppress the formation of the undesirable by-product, isobutyrophenone, a primary alcohol had the opposite effect, actually increasing the production of isobutyrophenone.

It was also found that water could be added to the reaction stream in the form of steam to suppress isobutyrophenone production. This is important for plant-scale production of propiophenone containing minimum amounts of isobutyrophenone. In plant-scale runs the effect of steam was even greater than for the bench-scale run so that production runs of propiophenone routinely contained from about 0.15 percent isobutyrophenone down to no measurable amount. This is important for pharmaceutical use where a limit of about 0.5% is required.

Surface-to-volume ratio of the reactor appeared to have no major effect on by-product formation.

In laboratory runs addition of water to the reaction stream resulted in a slight increase in another by-product, i.e., acetopheone. In the plant, however, acetophenone production was 1% or lower. Without steam addition, plant runs usually produced about 0.05 to about 0.1 pound of acetophenone per pound of propiophenone.

While isopropanol is more effective on a molar basis than water or steam in suppressing isobutyrophenone formation, it is not as economical.

Although the invention has been described in its preferred forms with a certain degree of particularity, it is understood that the present disclosure of the preferred forms has been made only by way of example and that numerous changes may be resorted to without departing from the spirit and scope of the invention.

What is claimed is:

1. In the process for production of propiophenone by the catalytic, vapor-phase, cross-decarboxylation of an aromatic carboxylic acid having 6 to about 14 carbon atoms with propionic acid, the improvement which comprises introducing at least about 0.5 to about 25 moles of a diluent selected from the class consisting of water or a secondary alcohol having 3 to about 6 carbon atoms per mol of aromatic carboxylic acid into a feed stream comprising a mol ratio of aromatic carboxylic acid:propionic acid of about 1:1 to about 1:10 prior to the entrance of said feed stream into a reaction zone maintained at a temperature of about 400° C. to about 600° C. whereby the formation of by-products is suppressed.

2. The process claimed in claim 1 wherein the aromatic carboxylic acid is benzoic acid.

3. Process claimed in claim 1 wherein the mole ratio of water to aromatic carboxylic acid is about 4:1 to about 8:1.

4. Process claimed in claim 1 wherein the mol ratio of aromatic carboxylic acid to propionic acid is about 1:2 to about 1:4.

5. Process claimed in claim 1 wherein the water is introduced into the reaction stream as steam.

6. Process claimed in claim 1 wherein the secondary alcohol is isopropanol.

7. Process claimed in claim 1 wherein the reaction zone temperature is about 440° to about 520° C.

8. Process claimed in claim 1 wherein the catalyst is calcium acetate supported on alumina.

9. Process claimed in claim 1 wherein the reaction stream is fed to the reaction zone at a rate of about 0.4–1.0 grams per gram of catalyst per hour.

* * * * *